US012609199B2

(12) United States Patent
Park et al.

(10) Patent No.: US 12,609,199 B2
(45) Date of Patent: Apr. 21, 2026

(54) MACHINE LEARNING METHOD OF NEURAL NETWORK PREDICTING MECHANISM OF ACTION OF DRUG, AND METHOD OF PREDICTING MECHANISM OF ACTION OF DRUG BY USING THE NEURAL NETWORK

(71) Applicant: VUNO INC., Seoul (KR)

(72) Inventors: Sejin Park, Yongin-si (KR); Wonmo Jeong, Seoul (KR); Weonjin Kim, Seoul (KR)

(73) Assignee: VUNO INC., Seoul (KR)

( * ) Notice: Subject to any disclaimer, the term of this patent is extended or adjusted under 35 U.S.C. 154(b) by 1359 days.

(21) Appl. No.: 17/207,750

(22) Filed: Mar. 22, 2021

(65) Prior Publication Data

US 2021/0295160 A1 Sep. 23, 2021

(30) Foreign Application Priority Data

Mar. 23, 2020 (KR) ........................ 10-2020-0035259

(51) Int. Cl.
*G16H 50/20* (2018.01)
*G06N 3/063* (2023.01)
(Continued)

(52) U.S. Cl.
CPC ............. *G16H 50/20* (2018.01); *G06N 3/063* (2013.01); *G06N 3/08* (2013.01); *G06T 7/0012* (2013.01);
(Continued)

(58) Field of Classification Search
CPC ........ G06N 3/063; G06N 3/08; G06N 3/0442; G06N 3/0455; G06N 3/09;
(Continued)

(56) References Cited

U.S. PATENT DOCUMENTS

| 10,365,340 B1 | 7/2019 | Lou et al. |
| 2018/0184102 A1 | 6/2018 | Navarrete Michelini et al. |

(Continued)

FOREIGN PATENT DOCUMENTS

| WO | 2017/192629 A1 | 11/2017 |

OTHER PUBLICATIONS

Yan-Bin Wang, et al., A deep learning-based method for drug-target interaction prediction based on long short-term memory neural network, BMC Medical Informatics and Decision Making, Jun. 11, 2019, vol. 20, No. 49, pp. 1-9.

(Continued)

*Primary Examiner* — Brent Johnston Hoover
(74) *Attorney, Agent, or Firm* — IP & T GROUP LLP

(57) ABSTRACT

A method for a computing device to predict an action mechanism of a drug from medical images of a subject is disclosed. The method includes, from a plurality of medical images obtained in time series, outputting first compressed data corresponding to the plurality of medical images, each of the first compressed data having a smaller size than a corresponding medical image, estimating second compressed data corresponding to a medical image at a next time point to time points at which the plurality of medical images have been captured, based on the first compressed data, and predicting the action mechanism of the drug for the subject by inputting the second compressed data to a neural network predicting the action mechanism of the drug.

17 Claims, 9 Drawing Sheets

(51) Int. Cl.
    *G06N 3/08*           (2023.01)
    *G06T 7/00*           (2017.01)
    *G16H 20/10*        (2018.01)
    *G16H 30/00*        (2018.01)

(52) U.S. Cl.
    CPC ............. G16H 20/10 (2018.01); G16H 30/00
        (2018.01); *G06T 2207/20084* (2013.01)

(58) Field of Classification Search
    CPC ........ G06T 2207/20084; G06T 7/0012; G16C
        20/10; G16C 20/70; G16H 20/10; G16H
        30/00; G16H 30/40; G16H 50/20; G16H
                              70/40
    See application file for complete search history.

(56)           References Cited

U.S. PATENT DOCUMENTS

| | | | |
|---|---|---|---|
| 2019/0164632 A1 | 5/2019 | Jung et al. | |
| 2020/0092565 A1* | 3/2020 | Watters .................. | G06N 3/044 |
| 2020/0337648 A1* | 10/2020 | Saripalli ............... | G06N 20/00 |

OTHER PUBLICATIONS

Nicha C. Dvornek, et al., Jointly Discriminative and Generative Recurrent Neural Networks for Learning from fMRI, Mach Learn Med Imaging, Oct. 10, 2019, vol. 11861, pp. 382-390.

Duk-In Jon, M.D., Ph.D., Applications of Functional Magnetic Resonance Imaging(fMRI) to the Research of Psychiatric Disorders, J Korean Neuropsychiatr Assoc vol. 41, No. 1, Jan. 2002, p. 46-60.

Nicha C. Dvornek, et al., Jointly Discriminative and Generative Recurrent Neural Networks for Learning from fMRI, Mach Learn Med Imaging, Oct. 10, 2019, vol. 11861, pp. 1-12.

Takashi Matsubara, et al., Deep Neural Generative Model of Functional MRI Images for Psychiatric Disorder Diagnosis, arXiv:1712. 06260v2, Apr. 12, 2019, pp. 1-12.

Haiqing Li, et al., A novel multi-target regression framework for time-series prediction of drug efficacy, Scientific Reports, Jan. 18, 2017, vol. 7, No. 40652, pp. 1-9.

* cited by examiner

100

$\{X_0, X_1, X_2 \dots X_t\}$ $\{Y_0, Y_1, Y_2 \dots Y_t\}$

FIG. 7

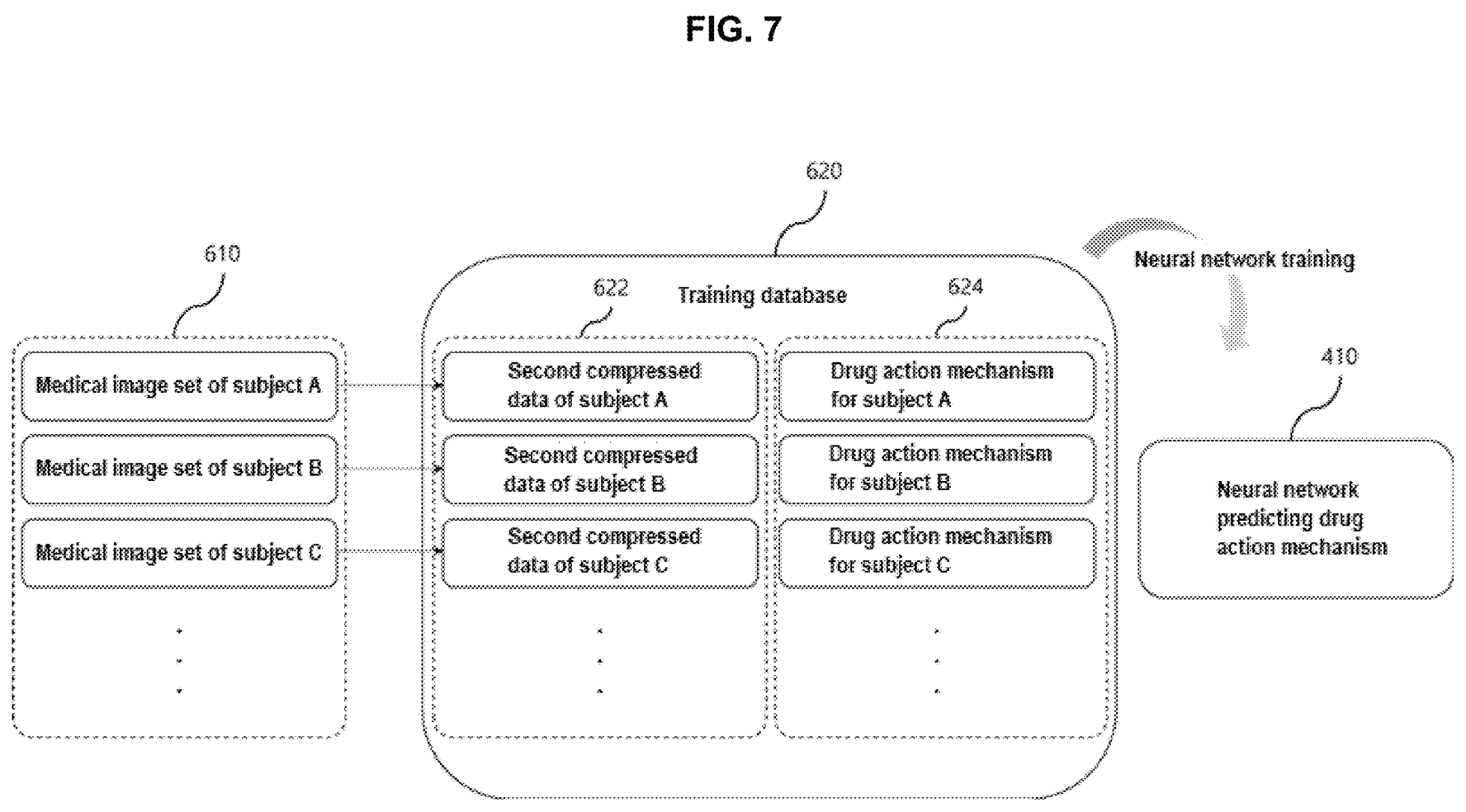

Neural network training

410

Neural network predicting drug action mechanism

620

Training database

624

Drug action mechanism for subject A

Drug action mechanism for subject B

Drug action mechanism for subject C

· · ·

622

Second compressed data of subject A

Second compressed data of subject B

Second compressed data of subject C

· · ·

610

Medical image set of subject A

Medical image set of subject B

Medical image set of subject C

· · ·

1

MACHINE LEARNING METHOD OF NEURAL NETWORK PREDICTING MECHANISM OF ACTION OF DRUG, AND METHOD OF PREDICTING MECHANISM OF ACTION OF DRUG BY USING THE NEURAL NETWORK

CROSS-REFERENCE TO RELATED APPLICATION

This application claims the benefit of Korean Patent Application No. 10-2020-0035259, filed on Mar. 23, 2020, which is hereby incorporated by reference as if fully set forth herein.

BACKGROUND

Field

The present disclosure relates to a method of training a neural network capable of predicting an action mechanism of a drug for a subject, a method of predicting the action mechanism of a drug for a subject by using the neural network, and an apparatus for performing the methods.

Discussion of the Related Art

In general, the action mechanism (simply, action) of a drug may vary depending on a patient's characteristics. A specific drug may work in some patients, but not in others. In another example, a specific drug may produce positive effects in some patients, but adverse effects or no significant effects in other patients. Particularly, drugs that treat mental or brain diseases have great differences in the action mechanisms for different patients, which makes it very difficult to find an appropriate drug for each patient. Accordingly, the process of searching for a drug suitable for each patient during treatment is regarded as a major obstacle to treatment of diseases.

Traditionally, a trial-and-error approach was used to search for drugs suitable for patients. That is, after a specific drug is administered to a patient, the patient is monitored to determine whether the drug is effective for a predetermined period of time, and according to the monitoring result, the drug is continuously administered or replaced with a new drug. However, with the trial-and-error approach, it takes a long time to monitor the drug efficacy.

In the case of mental illnesses or other brain diseases, magnetic resonance imaging (MRI) images of the brain are analyzed to observe the efficacy of a drug. However, medical images of a patient have to be monitored for a long time in order to confirm the drug efficacy, as described above. In the recent years, attempts have been made to analyze medical images by using artificial neural networks. However, because medical images obtained in time series to analyze drug efficacy are usually large in capacity, it is difficult to use them to train or use artificial neural networks.

SUMMARY

Provided are a method and apparatus for extracting easily analyzable data from medical images and training a neural network that predicts an action mechanism of a drug for a subject from the extracted data.

Provided are a method and apparatus for extracting easily analyzable data from medical images and predicting an action mechanism of a drug by using the extracted data and a trained neural network.

Additional aspects will be set forth in part in the description which follows and, in part, will be apparent from the description, or may be learned by practice of the presented embodiments of the disclosure.

According to one aspect, a machine learning method of a neural network predicting an action mechanism of a drug from medical images of a subject is provided, wherein the machine learning method includes: from a plurality of medical images $X_0, \ldots X_t$ obtained in time series, a computing device, outputting first compressed data $Z_0, \ldots Z_t$ corresponding to the plurality of medical images $X_0, \ldots X_t$, each of the first compressed data having a smaller capacity than a corresponding medical image, the computing device estimating second compressed data $h_{final}$ corresponding to a medical image at a next time point T (T>t) to time points at which the plurality of medical images $X_0, \ldots X_t$ have been captured, based on the first compressed data $Z_0, \ldots Z_t$, and the computing device training the neural network predicting the action mechanism of the drug for the subject by using the second compressed data $h_{final}$.

The computing device may generate a training database by repeating the outputting of first compressed data $Z_0, \ldots Z_t$ and the estimation of second compressed data $h_{final}$, by using a plurality of medical images $X_0, \ldots X_t$ obtained in time series from each of a plurality of different subjects, and the computing device trains the neural network predicting the action mechanism of the drug for the subject by using the training database.

The outputting of first compressed data $Z_0, \ldots Z_t$ may include performing a pre-treatment algorithm for each of the plurality of medical images $X_0, \ldots X_t$, and outputting the first compressed data $Z_0, \ldots Z_t$ so as to satisfy a condition that each of pre-treated medical images $Y_0, \ldots Y_t$ can be restored within a predetermined error range.

Each of the first compressed data $Z_0, \ldots Z_t$ may include a parameter for a probability distribution of a latent variable that enables restoration of a respective one of the pre-treated medical images $Y_0, \ldots Y_t$ within the predetermined error range.

The estimation of second compressed data $h_{final}$ may include: the computing device estimating the second compressed data $h_{final}$ by inputting the first compressed data $Z_0, \ldots Z_t$ to a recurrent neural network in an order corresponding to a time series order of the plurality of medical images $Z_0, \ldots Z_t$.

The estimation of the second compressed data $h_{final}$ may include: the computing device outputting intermediate data $h_0$ by inputting first compressed data $Z_0$ to the recurrent neural network, the computing device repeating the outputting of intermediate data $h_i$ by inputting first compressed data Zi and intermediate data $h_{i-1}$ to the recurrent neural network, for a period satisfying 0<i<t, while increasing a value of i, and the computing device estimating the second compressed data $h_{final}$ by inputting the first compressed data $Z_t$ and the intermediate data $h_{t-1}$ to the recurrent neural network.

According to another aspect, a method for a computing device to predict an action mechanism of a drug from medical images of a subject is provided, wherein the method includes: from a plurality of medical images $X_0, \ldots X_t$ obtained in time series, outputting first compressed data $Z_0, \ldots Z_t$ corresponding to the plurality of medical images $X_0, \ldots X_t$, each of the first compressed data having a smaller capacity than a corresponding medical image, estimating second compressed data $h_{final}$ corresponding to a medical image at a next time point T (T>t) to time points at which the plurality of medical images $X_0, \ldots X_t$ have been

3 captured, based on the first compressed data $Z_0, \ldots Z_t$, and predicting the action mechanism of the drug for the subject by inputting the second compressed data $h_{final}$ to a neural network predicting the action mechanism of the drug.

According to another aspect, a computing device that predicts an action mechanism of a drug is provided, wherein the computing device includes a communication unit and a processor coupled to the communication unit. The processor is configured to perform, from a plurality of medical images $X_0, \ldots X_t$ obtained in time series, a process of outputting first compressed data $Z_0, \ldots . Z_t$ corresponding to the plurality of medical images $X_0, \ldots X_t$, each of the first compressed data having a smaller capacity than a corresponding medical image, a process of estimating second compressed data $h_{final}$ corresponding to a medical image at a next time point T (T>t) to time points at which the plurality of medical images $X_0, \ldots X_t$ have been captured, based on the first compressed data $Z_0, \ldots . Z_t$, and a process of predicting the action mechanism of a drug for a subject by using the second compressed data $h_{final}$.

According to another aspect, a computer program product for predicting an action mechanism of a drug from medical images of a subject is provided, wherein the computer program product comprises a computer readable storage medium having program code embodied therein, and wherein the program code, when executed, performs operations, the operations comprising: from a plurality of medical images $X_0, \ldots X_t$ obtained in time series, outputting first compressed data $Z_0, \ldots . Z_t$ corresponding to the plurality of medical images $X_0, \ldots X_t$, each of the first compressed data having a smaller size than a corresponding medical image; estimating second compressed data $h_{final}$ corresponding to a medical image at a next time point T (T>t) to time points at which the plurality of medical images $X_0, \ldots X_t$ have been captured, based on the first compressed data $Z_0, \ldots . Z_t$; and predicting the action mechanism of the drug for the subject by inputting the second compressed data $h_{final}$ to a neural network predicting the action mechanism of the drug.

The neural network predicting an action mechanism of the drug may include a fully connected layer, and output one of predetermined result classes for the action mechanism of the drug by receiving the second compressed data $h_{final}$.

The outputting of first compressed data $Z_0, \ldots . Z_t$ may include performing a pre-treatment algorithm for each of the plurality of medical images $X_0, \ldots X_t$, and outputting the first compressed data $Z_0, \ldots . Z_t$ so as to satisfy a condition that each of pre-treated medical images $Y_0, \ldots Y_t$ can be restored within a predetermined error range.

Each of the first compressed data $Z_0, \ldots . Z_t$ may include a parameter for a probability distribution of a latent variable that enables restoration of a respective one of the pre-treated medical images $Y_0, \ldots Y_t$ within the predetermined error range.

The estimation of second compressed data $h_{final}$ may include: estimating the second compressed data $h_{final}$ by inputting the first compressed data $Z_0, \ldots . Z_t$ to a recurrent neural network in an order corresponding to a time series order of the plurality of medical images $Z_0, \ldots . Z_t$.

The estimation of the second compressed data $h_{final}$ may include: outputting intermediate data $h_0$ by inputting first compressed data $Z_0$ to the recurrent neural network, (repeatedly) outputting intermediate data $h_i$ by inputting first compressed data $Zi$ and intermediate data $h_{i-1}$ to the recurrent neural network, for a period satisfying 0<i<t, while increasing a value of i, and estimating the second compressed data $h_{final}$ by inputting the first compressed data $Z_t$ and the intermediate data $h_{t-1}$ to the recurrent neural network.

The neural network predicting the action mechanism of the drug may be in a state of being trained based on (i) a first training database including a plurality of second compressed data $h_{final}$ of another subjects and (ii) a second training database including action mechanism results of the drug for the another subjects.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings:

FIG. 7 is a conceptual diagram illustrating training of a neural network that predicts an action mechanism of a drug in the computing device;

DETAILED DESCRIPTION

Figure 1:
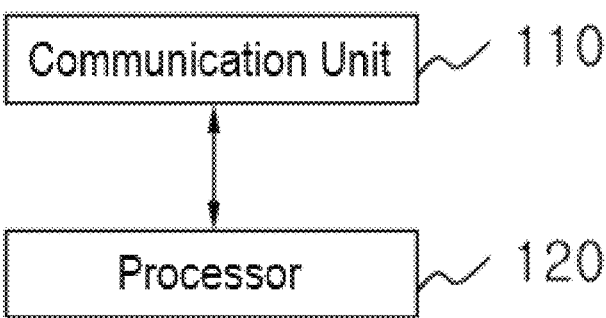
FIG. 1 is a conceptual diagram illustrating an exemplary configuration of a computing device that performs methods described in the present disclosure.

A detailed description will be given below of the present disclosure with reference to the accompanying drawings illustrating specific embodiments of the present disclosure to clarify the objects, technical solutions, and advantages of the present disclosure. These embodiments are described in detail enough to enable those skilled in the art to implement the present disclosure.

The term "image" or "image data" used throughout the detailed description and claims of the present disclosure refers to multi-dimensional data including discrete image elements (e.g., pixels in a two-dimensional (2D) image and voxels in a three-dimensional (3D) image).

"Medical image" refers to a medical image of a subject collected by (cone-beam) computed tomography, magnetic resonance imaging (MRI), ultrasound waves, or any other medical imaging system known in the art.

In the drawings, cone-beam computed tomography (CBCT) image data is shown as an exemplary imaging modality in the drawings, for convenience of description. However, those skilled in the art will understand that imaging modalities used in various embodiments of the present disclosure include, but not limited to, X-ray, MRI, CT, positron emission tomography (PET), PET-CT, single photon emission computed topography (SPECT), SPECT-CT, magnetic resonance-positron emission tomography (MR-PET), 3D ultrasound waves, and so on.

Those skilled in the art will understand that "training" or "learning" means machine learning based on procedural computing, not intended to refer to mental activities such as human educational activities throughout the detailed description and claims of the present disclosure.

Further, throughout the detailed description and claims of this disclosure, the word "comprise" and its variations are not intended to exclude other technical features, additions, components, or steps. Further, "one" or "a" is used to indicate one or more, and "another" is limited to at least a second.

Other objects, advantages, and features of the present disclosure will be apparent to those skilled in the art, in part, from this description, and in part from implementation of the present disclosure. The examples and drawings below are provided by way of example, not intended to limit the present disclosure. Therefore, the details of a specific structure or function in the present disclosure should not be construed as limiting. Rather, they should be interpreted as representative basic data that provide guidelines for a person skilled in the art to implement the present disclosure with any suitable detailed structure.

Moreover, the present disclosure covers all possible combinations of the embodiments shown in the disclosure. It should be understood that although various embodiments of the present disclosure are different from each other, they need not be mutually exclusive. For example, specific shapes, structures, and features described herein may be implemented as other embodiments without departing from the spirit and scope of the present disclosure in relation to one embodiment. In addition, it is to be understood that the positions or arrangements of individual components in each disclosed embodiment may be changed without departing from the spirit and scope of the present disclosure. Accordingly, the following detailed description is not intended to be taken in a limited sense, and the scope of the present disclosure, if properly described, is limited only by the appended claims, along with all scopes equivalent to those claimed by the claims. Like reference numerals denote the same or similar functions over several aspects in the drawings.

Unless otherwise indicated or clearly contradicting in the context, a singular expression includes plural referents. Further, lest it should obscure the subject matter of the present disclosure, a detail description of a known structure or function will be avoided herein.

Reference will be made to preferred embodiments of the present disclosure with reference to the accompanying drawings to allow those skilled in the art to easily implement the present disclosure.

FIG. 1 is a conceptual diagram illustrating an exemplary configuration of a computing device that performs methods described in the present disclosure.

A computing device 100 according to an exemplary embodiment may include a communication unit 110 and a processor 120, and communicate with an external computing device (not shown) directly or indirectly through the communication unit 110.

Specifically, the computing device 100 may achieve desired system performance by using a combination of typical computer hardware (e.g., a device that may include a computer processor, a memory, a storage, an input/output (I/O) device, and other components of an existing computing device, an electronic communication device such as a router and a switch, and an electronic information storage system such as a network-attached storage (NAS) and a storage area network (SAN)) and computer software (i.e., instructions that cause the computing device to operate in a specific manner).

In this computing device 100, the communication unit 110 may transmit and receive a request and a response to and from another computing device interworking with the computing device 100. For example, the request and the response may be transmitted and received in the same transmission control protocol (TCP) session, which should not be construed as limiting. For example, the request and the response may be transmitted and received in user datagram protocol (UDP) datagrams. In its broad sense, the communication unit 110 may include a keyboard that receives an instruction or an indication, a pointing device such as a mouse, other external input devices, a printer, a display, and other external output devices.

The processor 120 may include hardware components such as a micro processing unit (MPU), a central processing unit (CPU), a graphics processing unit (GPU) or tensor processing unit (TPU), a cash memory, and a data bus. The processor 120 may further include an operating system (OS) and software components of applications that serve specific purposes. The processor 120 may execute instructions for executing the functions of a neural network as described below.

Figure 2:
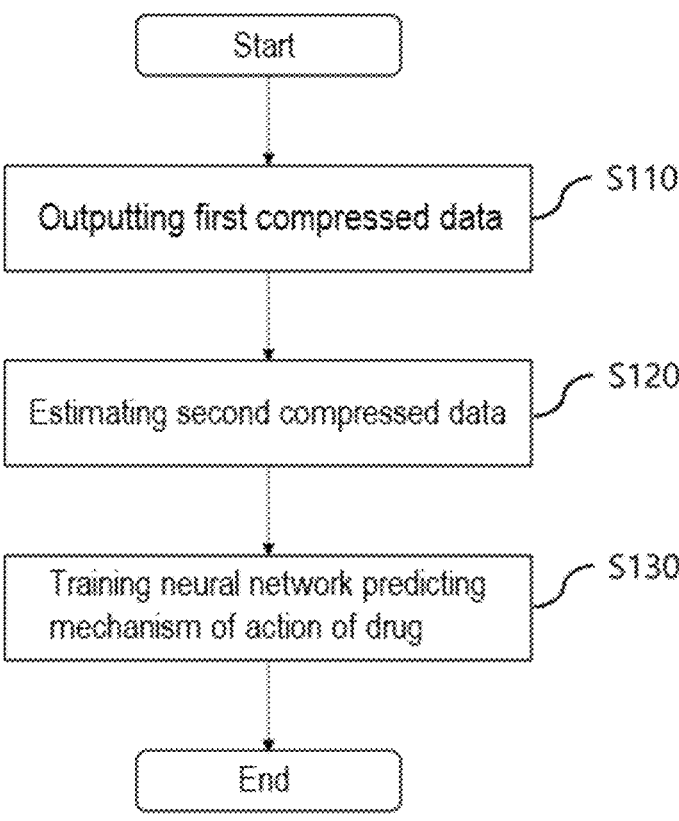
FIG. 2 is a flowchart illustrating a machine learning method of a neural network according to an exemplary embodiment.

FIG. 2 is a flowchart illustrating a machine learning method of a neural network according to an exemplary embodiment.

Referring to FIG. 2, the computing device 100 may output first compressed data from a plurality of medical images obtained in time series in step S110. The plurality of medical images may include images of a specific subject captured at a plurality of time points. For example, the plurality of medical images may include images of a specific part of the subject captured at a plurality of time points after a drug is administered to the subject. In another example, the plurality of medical images may include at least one image captured before a drug is administered to the subject and at least one image captured after the drug is administered to the subject.

For example, when a target drug of which the mechanism of action is to be monitored is used to treat mental disorders and other brain diseases including depressive disorder, the medical images may include an MRI image of the brain. The MRI image may include a functional magnetic resonance imaging (fMRI) image showing the blood flow or activity of brain tissues, to which the embodiment is not limited. The type of medical images may vary depending on the disease to be treated. For example, the medical images may include a T1 MRI image obtained by T1 enhancement and a T2 MRI image obtained by T2 enhancement in addition to the fMRI image. The medical images may include an X-ray image, a CT image, an MR-PET image, an ultrasound image, and so on in addition to an MRI image, to which the embodiment is not limited. Further, the medical images may include an image of a body part other than the brain of the subject.

Each of the first compressed data may correspond to one of the plurality of medical images. The first compressed data may represent the features of the medical images. The size/capacity of the first compressed data of a medical image may be smaller than that of the medical image. The computing device 100 may reconstruct the medical images corresponding to the first compressed data within a specific error range, from the first compressed data. The computing device 100 may output the first compressed data by using a specific neural network.

Figure 3:
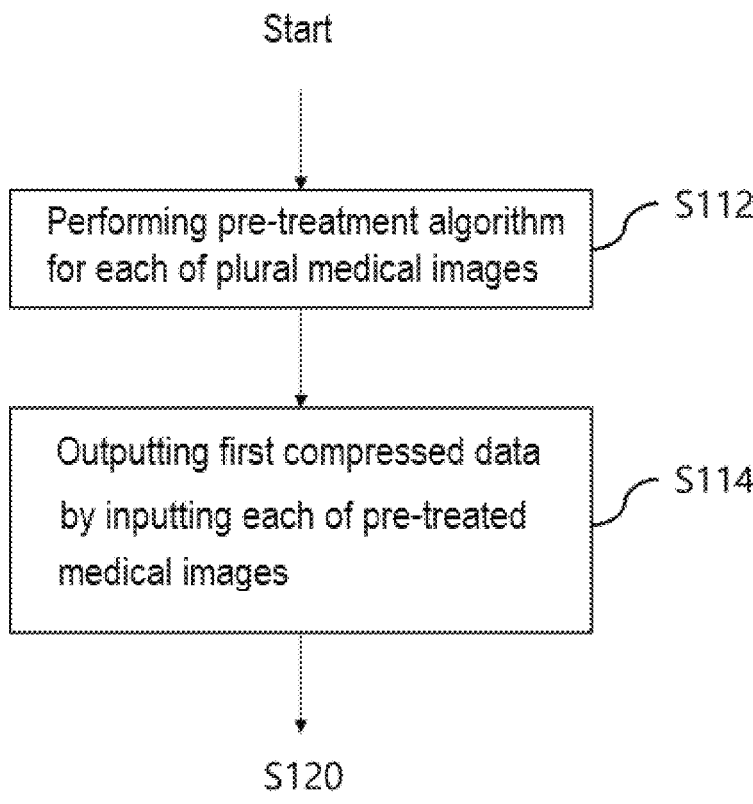
FIG. 3 is a detailed flowchart illustrating step S110 illustrated in FIG. 2.

FIG. 3 is a detailed flowchart illustrating step S110 illustrated in FIG. 2.

Referring to FIG. 3, the computing device 100 may perform a pre-treatment algorithm for each of the plurality of medical images in step S112. The computing device 100 may convert the plurality of medical images to a form which is easily analyzed by performing the pre-treatment algorithm. The pre-treatment algorithm may include, but not limited to, at least one of coregistration, affine transformation, and intensity normalization.

Figure 4:
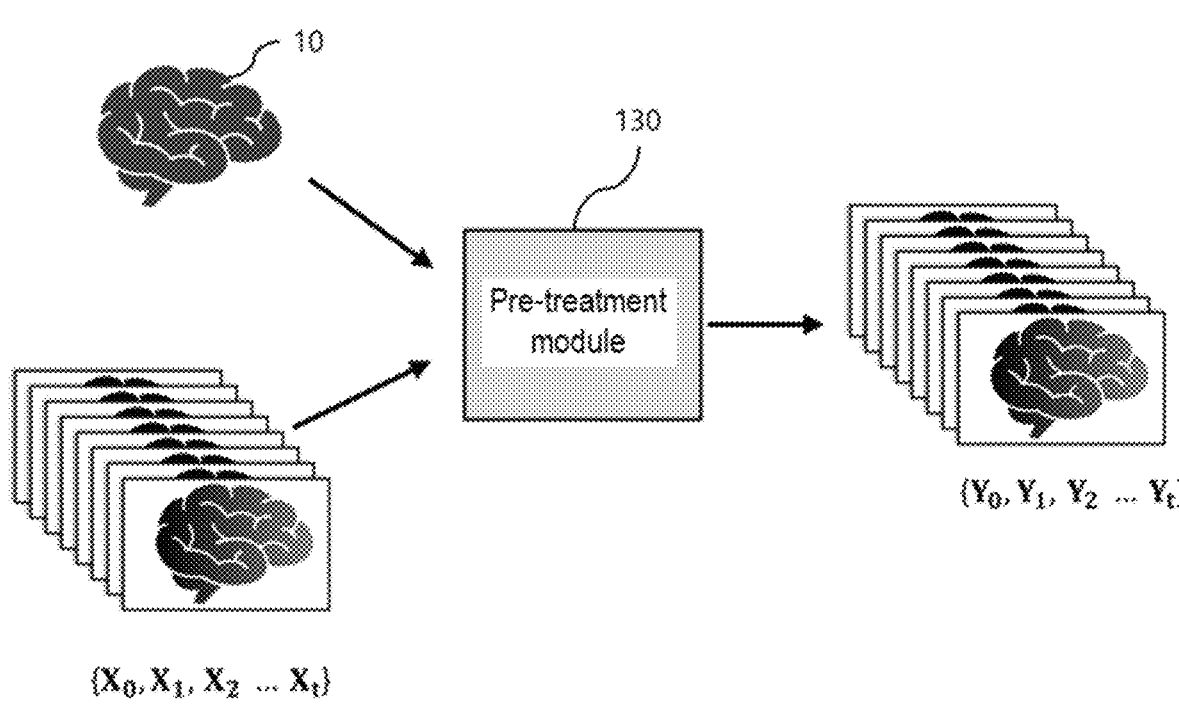
FIG. 4 is a conceptual diagram illustrating exemplary execution of a pre-treatment algorithm for each of a plurality of medical images in the computing device.

FIG. 4 is a conceptual diagram illustrating execution of a pre-treatment algorithm for each of a plurality of medical images in the computing device 100.

Referring to FIG. 4, a plurality of medical images $\{X_0, X_1, X_2 \ldots X_t\}$ may be images captured at different time points. t0, t1, t2, . . . are indexes indicating the time points at which the medical images have been captured. $X_0$ represents a medical image captured at a $0^{th}$ time point, $X_1$ represents a medical image captured at a $1^{st}$ time point, $X_2$ represents a medical image captured at a $2^{nd}$ time point, and $X_t$ represents a medical image captured at a $t^{th}$ time point. Unnecessary differences may be produced between the medical images due to different capturing angles, different capturing environments, and other different capturing settings. The differences between the medical images may act as an obstacle to analysis of the medical images obtained in time series. Accordingly, the computing device 100 may reduce the unnecessary differences among medical images $\{X_{t0}, X_{t1}, X_{t2} \ldots \}$ and convert the medical images $\{X_{t0}, X_{t1}, X_{t2} \ldots \}$ to a form that allows easy analysis, by performing the pre-treatment algorithm for the respective medical images $\{X_0, X_1, X_2 \ldots X_t\}$.

The computing device 100 may determine a medical image captured at any one time point as a medical image at a reference time point from among the medical images $\{X_0, X_1, X_2 \ldots X_t\}$. The computing device 100 may coregister the medical image (e.g., $X_1$) at the reference time point with another medical image 10 of the subject. The medical image 10 may be, for example, a medical image captured in a different capturing scheme from the medical images $\{X_0, X_2 \ldots X_t\}$. For example, the medical images $\{X_0, X_1, X_2 \ldots X_t\}$ may include fMRI images, and the medical image 10 may include a T1 MRI image (e.g., a 3D T1w brain image) captured in a T1 scheme. The MRI image captured in the T1 scheme may be, but not limited to, an image representing a tissue having a short T1 relaxation time with high signal strength. For example, the medical image 10 may include a T2 MRI image representing a tissue having a short T2 relaxation time with high signal strength.

The computing device 100 may coregister the medical image (e.g., $X_1$) at the reference time in a manner that minimizes a cost function dependent on the difference between the medical image at the reference time point and the other medical image 10. The computing device may coregister each of the medical images at the remaining time points (e.g., $X_0, X_2 \ldots X_t$) with respect to the medical image at the reference time point. The computing device 100 may convert the medical images $\{X_0, X_1, X_2 \ldots X_t\}$ to a form that allows easy analysis through coregistration of the medical images $\{X_0, X_1, X_2 \ldots X_t\}$.

The computing device 100 may perform affine transformation on each of the medical images $\{X_0, X_1, X_2 \ldots X_t\}$. Affine transformation may include geometric transformation that preserves the properties of a straight line, a simple ratio, and parallel lines in an image. The computing device 100 may correct the differences in capturing direction or capturing angle among the medical images $\{X_0, X_1, X_2 \ldots X_t\}$ by affine transformation.

The computing device 100 may normalize the intensity of each of the medical images $\{X_0, X_1, X_2 \ldots X_t\}$. The computing device 100 may correct signal strength differences among the medical images $\{X_0, X_1, X_2 \ldots X_t\}$ by the intensity normalization.

The computing device may obtain pre-treated medical images $\{Y_0, Y_1, Y_2 \ldots Y_t\}$ by performing the pre-treatment algorithm.

According to an embodiment, the step of performing a pre-treatment algorithm may be skipped. For example, when the computing device 100 obtains medical images which have already been pre-treated by the pre-treatment algorithm, the computing device 100 may skip the step of performing a pre-treatment algorithm. In another example, when medical images are not significantly different from each other and are easily analyzable even without pre-treatment, the computing device 100 may skip the step of performing a pre-treatment algorithm With reference made to FIG. 3 again, the computing device 100 may input the pre-treated medical images $\{Y_0, Y_1, Y_2 \ldots Y_t\}$ to an encoder and thus output the first compressed data in step S114.

Figure 5:
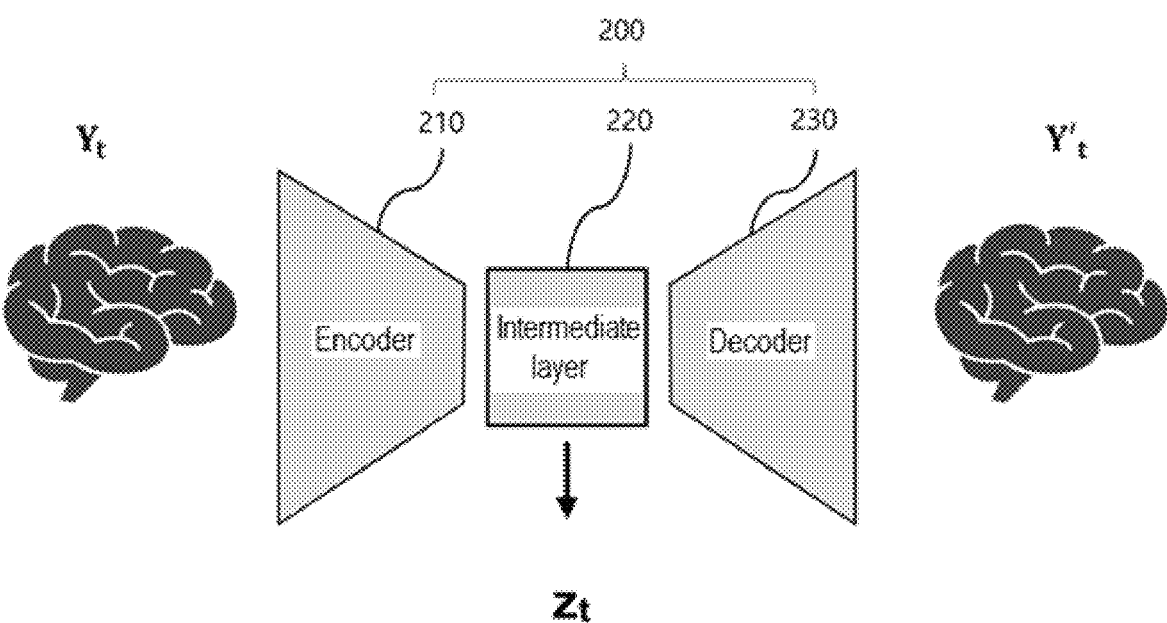
FIG. 5 is a conceptual diagram illustrating output of first compressed data in the computing device.

FIG. 5 is a conceptual diagram illustrating output of the first compressed data in the computing device 100.

Referring to FIG. 5, the computing device 100 may train a specific neural network 200 to output the first compressed data. The specific neural network 200 may include, but not limited to, at least one of an auto-encoder, a denoising auto-encoder, or a variational auto-encoder. For example, the neural network 200 may include a different type of neural network that extracts the features of input image data. The following description will be given in the context of the neural network 200 including a variational auto-encoder, by way of example.

The neural network 200 may include an encoder 210, an intermediate layer 220, and a decoder 230. The encoder 210 may receive the pre-treated medical images. In FIG. 5, $Y_t$ represents a pre-treated image of the medical image $X_t$ captured at the $t^{th}$ time point. When the computing device 100 skips the step of performing a pre-treatment algorithm as described before, the medical image $X_t$ may be input to the encoder 210.

For the input of the pre-treated medical image $Y_t$, the encoder 210 may output first compressed data that enables reconstruction of the pre-treated medical image $Y_t$ within a specific error range. For example, the first compressed data may include information about a latent variable $Z_t$ that enables reconstruction of the pre-treated medical image $Y_t$ within the specific error range. The first compressed data may include parameters for the probability distribution of the latent variable $Z_t$. For example, assuming that the probability distribution of the latent variable $Z_t$ is simplified to a Gaussian distribution, the first compressed data includes information about a mean and a variance that may define the Gaussian distribution of the latent variable $Z_t$.

The encoder 210 may output the information about the mean and variance of the latent variable $Z_t$. The intermediate layer 220 may transmit data randomly sampled from the Gaussian distribution determined by the mean and variance to the decoder 230. Since the intermediate layer 220 may sample different data each time, even after the training of the neural network 200 is finished, the output data of the neural network 200 may be slightly different for the same input data. The decoder 230 may reconstruct an image by using the data received from the intermediate layer 220. The decoder 230 may output a reconstructed image $Y'_t$.

The computing device 100 may train the neural network 200 in a manner that reduces the difference between the medical image $Y_t$ input to the encoder 210 and the reconstructed image $Y'_t$ output from the decoder 230. When the condition that the difference between the medical image $Y_t$ and the reconstructed image $Y'_t$ is less than a predetermined allowed error range is satisfied, the computing device 100 may determine that the neural network 200 has been sufficiently trained. Upon completion of the training of the neural network 200, the computing device 100 may output the first compressed data by using the encoder 210 of the neural network 200. The computing device 100 may output the first compressed data corresponding to each of the pre-treated medical images.

With reference made to FIG. 2 again, the computing device 100 may estimate second compressed data corresponding to a medical image at a time point after the plurality of medical images have been captured, based on the first compressed data in step S120.

Figure 6:
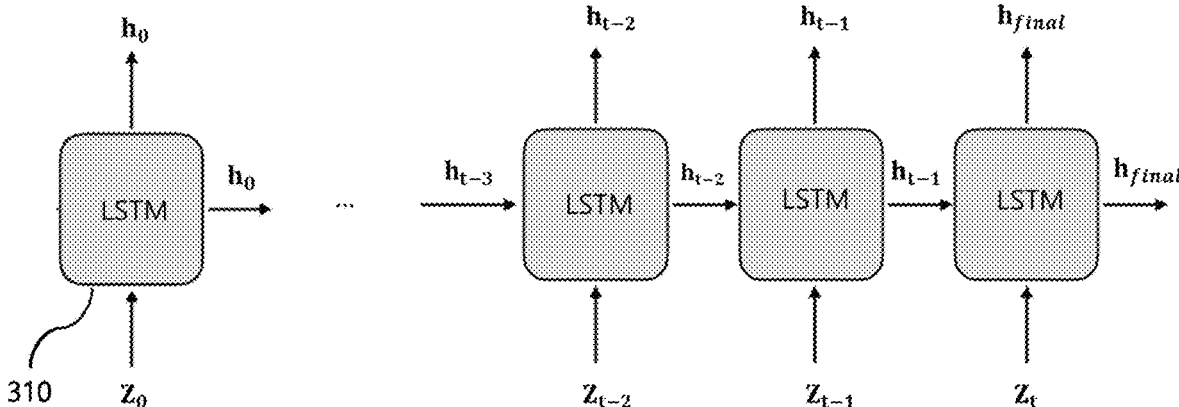
FIG. 6 is a conceptual diagram illustrating estimation of second compressed data in the computing device.

FIG. 6 is a conceptual diagram illustrating estimation of the second compressed data in the computing device 100.

Referring to FIG. 6, the computing device 100 may estimate the second compressed data based on the first compressed data. The computing device 100 is shown in FIG. 6 as using a long short term memory neural network (LSTM) 310, to which the embodiment is not limited. The computing device 100 may estimate the second compressed data by using a recurrent neural network (RNN). The RNN may include an LSTM, a gated recurrent unit (GRU), and the like.

In FIG. 6, $Z_t$ represents the first compressed data corresponding to the medical image captured at the $t^{th}$ time point. For example, the intermediate layer 220 and the decoder 230 illustrated in FIG. 5 may output the image $Y'_t$ which is reconstructed from the medical image $Y_t$ obtained by pre-treating the medical image $X_t$ captured at the $t^{th}$ time point within a predetermined error range, by using the first compressed data $Z_t$. In another example, the intermediate layer 220 and the decoder 230 may output an image $X'_t$ which is reconstructed from the medical image $X_t$ captured at the $t^{th}$ time point within a predetermined error range, by using the first compressed data $Z_t$.

The computing device 100 may input the first compressed data $Z_0$, corresponding to the medical image captured at the $0^{th}$ time point, to the LSTM 310. For the input of the first compressed data $Z_0$, the LSTM 310 may output $h_0$. $h_0$ may represent the estimation result about compressed data corresponding to a medical image captured at a time point after the $0^{th}$ time point in the LSTM 310.

The computing device 100 may repeat an operation of estimating new second compressed data corresponding to a medical image captured at the next time by inputting (i) a second compressed data output from the LSTM 310 in a previous stage and (ii) new first compressed data to the LSTM 310. For example, the computing device 100 may output new second compressed data $h_{t-1}$ by inputting (i) the second compressed data $h_{t-2}$ which has been obtained by inputting $Z_{t-2}$ and $h_{t-3}$ to the LSTM 310, and (ii) the first compressed data $Z_{t-1}$ corresponding to the medical image captured at time t–1 to the LSTM 310.

Finally, the computing device 100 may estimate second compressed data $h_{final}$ based on the first compressed data $Z_t$ corresponding to the medical image captured at the last time point. $h_{final}$ may represent a result of predicting a change in the first compressed data $Z_t$ by the computing device 100. Accordingly, the computing device 100 may estimate $h_{final}$ as compressed data of a medical image expected to be obtained at a time point after the plurality of medical images are captured. $h_{final}$ may be the compressed data corresponding to the medical image expected to be obtained at the next time point, T after the $t^{th}$ time point at which the medical image $X_t$ has been captured. The time interval between the next time point T and the $t^{th}$ time point may not be equal to the time interval between the $t^{th}$ time point and the $(t-1)^{th}$ time point. For example, the time interval between the next time point T and the $t^{th}$ time point may be greater than the time interval between the $t^{th}$ time point and the $(t-1)^{th}$ time point. In another example, the time interval between the next time point T and the $t^{th}$ time point may be less than the time interval between the $t^{th}$ time point and the $(t-1)^{th}$ time point. In another example, the time interval between the next time point T and the $t^{th}$ time point may be equal to the time interval between the $t^{th}$ time point and the $(t-1)^{th}$ time point. The time interval between the next time point T and the $t^{th}$ time point may vary according to a target drug or a target disease.

Referring back to FIG. 2, the computing device 100 may train the neural network that predicts the action mechanism of a drug by using the second compressed data estimated using the LSTM 310. The computing device 100 may store the second compressed data of each of subjects in a training database by repeating steps S110 and S120 of FIG. 2 for different subjects. The computing device 100 may train the neural network that predicts the action mechanism of a drug by using the training database.

FIG. 7 is a conceptual diagram illustrating exemplary training of a neural network 410 in the computing device 100.

Referring to FIG. 7, the computing device 100 may estimate the second compressed data of each of a plurality of subjects from a set of medical images of the subject. For example, the computing device 100 may capture subject A and estimate the second compressed data of subject A by using medical images obtained in time series. Likewise, the computing device 100 may estimate the second compressed data of subject B by using medical images of subject B obtained in time series. The computing device 100 may build a training database 620 by using the second compressed data obtained by analyzing the medical images of a plurality of subjects.

The training database 620 includes a first training database 622 including information about the second compressed data of subjects and a second training database 624 including information about results of the action mechanism of a drug for the subjects.

The computing device 100 may train the neural network 410 that predicts the action mechanism of a drug by using the training database 620. The neural network 410 may include a fully connected layer. The neural network 410 may be trained to receive the second compressed data of the subject and output a prediction result of action mechanism of the drug for the subject. For example, the computing device 100 may train the neural network 410 by a supervised training method using the second compressed data of subjects and information about actual results of action mechanisms of drug for the subjects, to which the embodiment is not limited. The computing device 100 may train the neural network 410 using other machine learning methods such as unsupervised training and reinforcement training. The configuration of the training database 620 may be changed according to a manner in which the computing device 100 trains the neural network 410. For example, when the computing device 100 trains the neural network 410 in an unsupervised manner, the training database 620 includes only the first training database 622 without the second training database 624.

The method of training the neural network 410 to predict the action mechanism of a drug by the computing device 100 has been described above. According to the above-described embodiment, the computing device 100 may estimate second compressed data from medical images obtained in time series. The use of first compressed data having a smaller size/capacity than that of the medical images from the medical images in the computing device 100 may facilitate estimation of second compressed data. In addition, since the computing device 100 uses the second compressed data having a size/capacity smaller than that of the medical images as training data for the neural network 410, the neural network 410 may be trained simply and easily. Furthermore, since the computing device 100 outputs compressed data that enables restoration of the medical images within a predetermined error range, the reliability of the result of training the neural network 410 may be increased.

Figure 8:
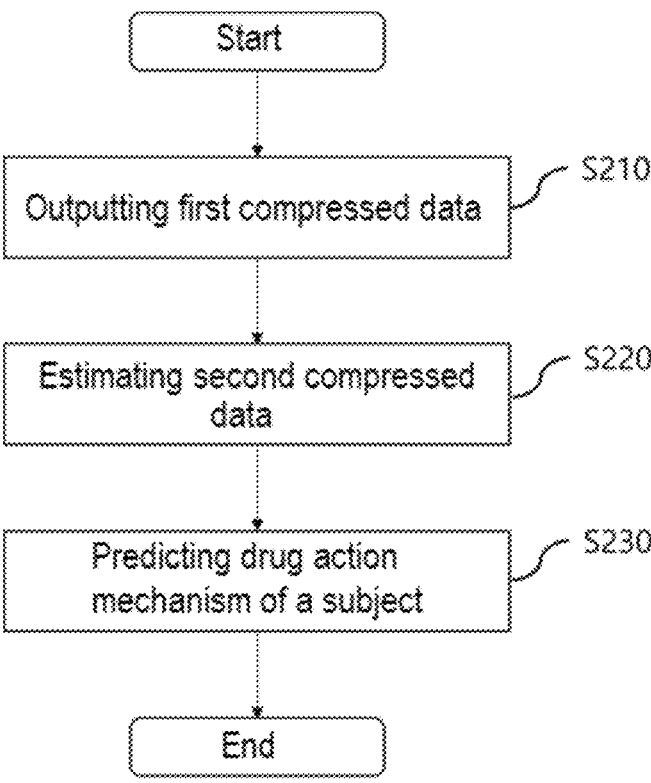
FIG. 8 is a flowchart illustrating a method of predicting an action mechanism of a drug in the computing device according to an exemplary embodiment.

FIG. 8 is a flowchart illustrating a method of predicting the action mechanism of a drug by the computing device 100 according to an exemplary embodiment.

A redundant description of FIG. 8 with the description of FIGS. 2 to 7 will be avoided herein. Referring to FIG. 8, the computing device 100 may estimate second compressed data from medical images of a subject in steps S210 and S220 based on the embodiments described with reference to FIGS. 2 to 7.

In step S230, the computing device 100 may predict an action mechanism of a drug for the subject by using the second compressed data.

Figure 9:
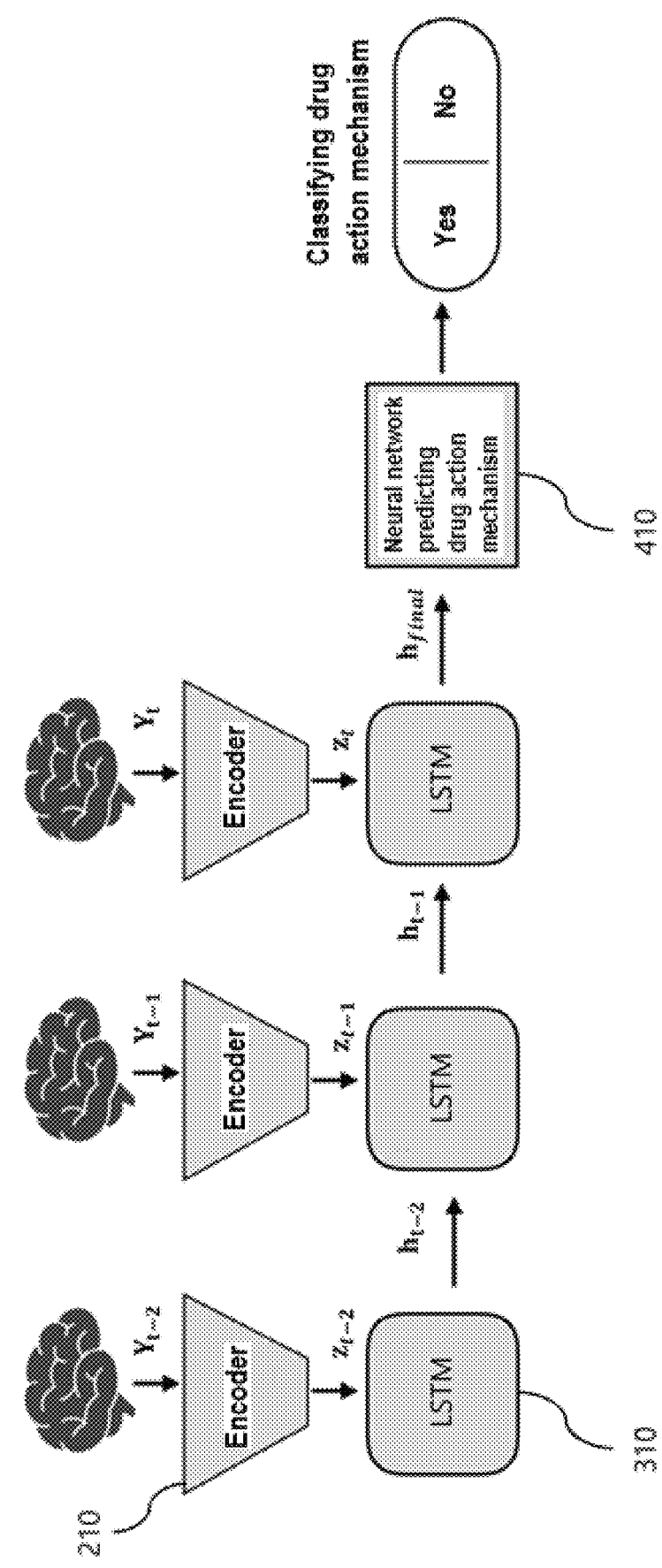
FIG. 9 is a conceptual diagram illustrating prediction of an action mechanism of a drug in the computing device.

FIG. 9 is a conceptual diagram illustrating prediction of the action mechanism of a drug for a subject in the computing device 100.

Referring to FIG. 9, the computing device 100 may predict the action mechanism of a drug by using the neural network 410. The neural network 410 may include a fully connected layer. It may be assumed that the neural network 410 has already been trained according to the method described with reference to FIGS. 2 to 7. The neural network 410 may receive second compressed data and output a prediction result of the action mechanism of a drug for the subject. The neural network 410 may output one of predetermined result classes for the action mechanism of the drug for the subject. For example, the neural network 410 may determine and output the prediction result of the action mechanism of the drug as one of classes 'Yes' (or, effective, present) and 'No' (or, ineffective, absent), to which the embodiment is not limited. The prediction result of the action mechanism of the drug may be classified differently. For example, the classes representing prediction results of the action mechanism of a drug may include 'positive' and 'negative'. In another example, three or more classes may be defined to represent the prediction result of the action mechanism of a drug. For example, the prediction result of the action mechanism of the drug may be represented as one of "positive", "negative", and "no response".

The computing device 100 may obtain the pre-treated medical images $\{Y_0, Y_1, Y_2 \ldots Y\}$ by performing the pre-treatment algorithm on each of the medical images obtained in time series. The computing device 100 may input the pre-treated medical images $\{Y_0, Y_1, Y_2 \ldots Y_t\}$ to the encoder 210 and output the first compressed data $\{Z_0, Z_1, Z_2 \ldots Z_t\}$. The computing device may sequentially input the first compressed data $\{Z_0, Z_1, Z_2 \ldots Z_t\}$ to the LSTM 310 to estimate the second compressed data $h_{final}$ which is compressed data expected to be obtained after the first compressed data $Z_t$ at the last time point. The computing device 100 may input the second compressed data $h_{final}$ to the neural network 410. The neural network 410 may output a prediction result for the action mechanism of the drug.

The method of training the neural network 410 to predict the action mechanism of a drug by the computing device 100 has been described above. According to the above-described embodiment, the computing device 100 may estimate second compressed data from medical images obtained in time series. Use of first compressed data having a smaller capacity than that of the medical images from the medical images in the computing device 100 may facilitate estimation of second compressed data. In addition, since the computing device 100 inputs the second compressed data having a capacity smaller than that of the medical images to the neural network 410, the neural network 410 may easily output a prediction result of the action mechanism of a drug.

As is apparent from the foregoing description, according to at least one embodiment, the computing device may estimate second compressed data from medical images obtained in time series. According to at least one embodiment, since the computing device uses the second compressed data having a smaller capacity than that of the medical images as training data for a neural network, the neural network may be trained simply and easily. According to at least one embodiment, because the computing device inputs the second compressed data having a smaller capacity than that of the medical images to the neural network, the network may easily output a result of predicting the action mechanism of a drug. According to at least one embodiment, the computing device may output compressed data in a manner that restores the medical images within a predetermined error rage, thereby increasing the reliability of the result of training the neural network and the output result of the neural network.

Those skilled in the art will clearly understand based on the description of the above embodiment that the method and/or processes of the present disclosure and the steps thereof may be implemented in hardware, software, or any combination of hardware and software suitable for a specific application. The hardware may include a general-purpose computer and/or a dedicated computing device or a specific computing device or special features or components of a specific computing device. The processes may be implemented by one or more microprocessors, microcontrollers, embedded microcontrollers, programmable digital signal processors, or other programmable devices, which include an internal and/or external memory. Additionally or alternatively, the processes may be implemented with specific integrated circuits (ASICs), programmable gate arrays, programmable array logic (PALs), or any other device or a combination of devices configured to process electronic signals. Furthermore, objects of the technical solution of the present disclosure or parts contributing to the prior art may be implemented in the form of program instructions executed through various computer components and recorded in a machine-readable recording medium. The machine-readable recording medium may include program instructions, data files, or data structures, alone or in combination. The program instructions recorded in the machine-readable recording medium may be specially designed and configured for the present disclosure, or may be known and available to a person skilled in the field of computer software. Examples of the machine-readable recording medium include magnetic media such as hard disks, floppy disks and magnetic tapes, optical recording media such as compact disk-read only memories (CD-ROMs), digital versatile disks (DVDs), and Blu-rays, and magneto-optical media such as floptical disks, and a hardware device specially configured to store and execute program instructions such as ROM, RAM, flash memory, and the like. The program instructions may be made in a structured programming language such as C, an object-oriented programming language such as C++, or a high-level or low-level programming language (assembly languages, hardware description languages, and database programming languages and technologies), including a machine language code, a byte code, and a premium language code that can be executed by a computer, using an interpreter, which may be stored and compiled or interpreted to be executed in a processor, a processor architecture, a heterogeneous combination of different hardware and software combinations, or a machine capable of executing any other program instructions, as well as any one of the afore-mentioned devices.

Therefore, in an aspect of the present disclosure, when the above-described methods and combinations thereof are performed by one or more computing devices, the methods and combinations thereof may be implemented as executable code that performs each step. In another aspect, the methods may be implemented as systems that perform the steps. The methods may be distributed across devices in various ways or all functions may be integrated into one dedicated, standalone device or other hardware. In another aspect, means for performing steps associated with the processes described above may include any hardware and/or software described above. All such sequential combinations and combinations are intended to be within the scope of the present disclosure.

For example, the hardware device may be configured to operate as one or more software modules to perform a processing according to the present disclosure, or vice versa. The hardware device may include a processor such as an MPU, a CPU, a GPU, or a TPU, which is coupled with a memory such as ROM/RAM for storing program instructions and configured to execute instructions stored in the memory, and may include a communication unit that exchanges signals with an external device. In addition, the hardware device may include a keyboard, a mouse, and other external input devices for receiving instructions written by developers.

While the present disclosure has been described with particular details such as specific elements and limited embodiments and drawings, this is provided only to help a more general understanding of the present disclosure, not limiting the present disclosure. Those skilled in the art may make various modifications and variations from this description.

Therefore, the spirit of the present disclosure is not limited to the above-described embodiments, and the appended claims and all equal or equivalent modifications to the claims fall within the scope of the spirit of the present disclosure.

The equal or equivalent modifications may include, for example, logically equivalent methods capable of producing the same result as that of carrying out the method according to the present disclosure. The intention and scope of the present disclosure are not to be limited by the examples described above, but should be understood in the broadest possible sense allowed by law.

What is claimed is:

1. A method of predicting an action mechanism of a drug from medical images of a subject by a computing device, the method comprising:

from a plurality of medical images $X_0, \ldots X_t$ obtained in time series, outputting first compressed data $Z_0, \ldots Z_t$ corresponding to the plurality of medical images $X_0, \ldots X_t$, each of the first compressed data having a smaller size than a corresponding medical image, wherein the plurality of medical images $X_0, \ldots X_t$ are the medical images related to a brain of the subject;

estimating second compressed data $h_0$ by inputting first compressed data $Z_0$ to a recurrent neural network;

estimating second compressed data $h_i$ corresponding to a predicted medical image $X'_{i+1}$ at a time point i+1 after a time point i at which a medical image $X_i$ was captured by inputting first compressed data $Z$; and second compressed data $h_{i-1}$ to the recurrent neural network, for a period satisfying $0 < i \leq t$, while increasing a value of i; and predicting the action mechanism of the drug for the subject by inputting second compressed data $h_t$ to a neural network learned to predict the action mechanism of the drug, wherein the second compressed data $h_t$ corresponds to a predicted medical image $X'_{t+2}$ which reflects a change in a blood flow of the brain or an activity of the brain predicted to occur at a time point t+1 after a time point t.

2. The method according to claim 1, wherein the neural network predicting the action mechanism of the drug includes a fully connected layer, and outputs one of predetermined result classes for the action mechanism of the drug by receiving the second compressed data $h_t$.

3. The method according to claim 1, wherein the outputting of first compressed data $Z_0, \ldots Z_t$ comprises:

performing a pre-treatment algorithm for each of the plurality of medical images $X_0, \ldots X_t$; and outputting the first compressed data $Z_0, \ldots Z_t$ so as to satisfy a condition that each of pre-treated medical images $Y_0, \ldots Y_t$ can be restored within a predetermined error range.

4. The method according to claim 3, wherein each of the first compressed data $Z_0, \ldots Z_t$ includes a parameter for a probability distribution of a latent variable that enables restoration of a respective one of the pre-treated medical images $Y_0, \ldots Y_t$ within the predetermined error range.

5. The method according to claim 1, wherein the estimation of second compressed data $h_t$ comprises:

estimating the second compressed data $h_t$ by inputting the first compressed data $Z_0, \ldots Z_t$ to a recurrent neural network in an order corresponding to a time series order of the plurality of medical images $X_0, \ldots X_t$.

6. The method according to claim 1, wherein the neural network predicting the action mechanism of the drug is in a state of being trained based on (i) a first training database including a plurality of second compressed data $h_t$ of another subjects and (ii) a second training database including action mechanism results of the drug for the another subjects.

7. A computing device comprising:

a communication unit; and a processor coupled to the communication unit, wherein the processor is configured to perform processes including:

from a plurality of medical images $X_0, \ldots X_t$ obtained in time series, outputting first compressed data $Z_0, \ldots Z_t$ corresponding to the plurality of medical images $X_0, \ldots X_t$, each of the first compressed data having a smaller capacity than a corresponding medical image, wherein the plurality of medical images $X_0, \ldots X_t$ are the medical images related to a brain of the subject;

estimating second compressed data $h_0$ by inputting first compressed data $Z_0$ to a recurrent neural network;

estimating second compressed data $h_1$ corresponding to a predicted medical image $X'_{i+1}$ at a time point i+1 after a time point i at which a medical image $X_i$ was captured by inputting first compressed data Z; and second compressed data $h_{i-1}$ to the recurrent neural network, for a period satisfying 0<i≤t, while increasing a value of i; and predicting the action mechanism of a drug for a subject by inputting second compressed data $h_t$ to a neural network learned to predict the action mechanism of the drug, wherein the second compressed data $h_t$ corresponds to a predicted medical image $X'_{t+1}$, which reflects a change in a blood flow of the brain or an activity of the brain predicted to occur at a time point t+1 after a time point t.

8. The computing device according to claim 7, wherein the neural network predicting the action mechanism of the drug includes a fully connected layer, and outputs one of predetermined result classes for the action mechanism of the drug by receiving the second compressed data $h_t$.

9. The computing device according to claim 7, wherein the outputting of first compressed data $Z_0, \ldots Z_t$ comprises:

performing a pre-treatment algorithm for each of the plurality of medical images $X_0, \ldots X_t$; and outputting the first compressed data $Z_0, \ldots Z_t$ so as to satisfy a condition that each of pre-treated medical images $Y_0, \ldots Y_t$ can be restored within a predetermined error range.

10. The computing device according to claim 9, wherein each of the first compressed data $Z_0, \ldots Z_t$ includes a parameter for a probability distribution of a latent variable that enables restoration of a respective one of the pre-treated medical images $Y_0, \ldots Y_t$ within the predetermined error range.

11. The computing device according to claim 7, wherein the estimation of second compressed data $h_t$ comprises:

estimating the second compressed data $h_t$ by inputting the first compressed data $Z_0, \ldots Z_t$ to a recurrent neural network in an order corresponding to a time series order of the plurality of medical images $X_0, \ldots X_t$.

12. The computing device according to claim 7, wherein the neural network predicting the action mechanism of the drug is in a state of being trained based on (i) a first training database including a plurality of second compressed data $h_t$ of another subjects and (ii) a second training database including action mechanism results of the drug for the another subjects.

13. A non-transitory computer program product for predicting an action mechanism of a drug from medical images of a subject, wherein the computer program product comprises a computer readable storage medium having program code embodied therein, and wherein the program code, when executed, performs operations, the operations comprising:

from a plurality of medical images $X_0, \ldots X_t$ obtained in time series, outputting first compressed data $Z_0, \ldots Z_t$ corresponding to the plurality of medical images $X_0, \ldots X_t$, each of the first compressed data having a smaller size than a corresponding medical image, wherein the plurality of medical images $X_0, \ldots X_t$ are the medical images related to a brain of the subject;

estimating second compressed data $h_0$ by inputting first compressed data $Z_0$ to a recurrent neural network;

estimating second compressed data $h_1$ corresponding to a predicted medical image $X'_{i+1}$ at a time point i+1 after a time point i at which a medical image $X_i$ was captured by inputting first compressed data Z; and second compressed data $h_{i-1}$ to the recurrent neural network, for a period satisfying 0<i≤t, while increasing a value of i; and predicting the action mechanism of the drug for the subject by inputting second compressed data $h_t$ to a neural network learned to predict the action mechanism of the drug, wherein the second compressed data $h_t$ corresponds to a predicted medical image $X'_{t+1}$, which reflects a change in a blood flow of the brain or an activity of the brain predicted to occur at a time point t+1 after a time point t.

14. The computer program product according to claim 13, wherein the neural network predicting the action mechanism of the drug includes a fully connected layer, and outputs one of predetermined result classes for the action mechanism of the drug by receiving the second compressed data $h_t$.

15. The computer program product according to claim 13, wherein the outputting of first compressed data $Z_0, \ldots Z_t$ comprises:

performing a pre-treatment algorithm for each of the plurality of medical images $X_0, \ldots X_t$; and outputting the first compressed data $Z_0, \ldots Z_t$ so as to satisfy a condition that each of pre-treated medical images $Y_0, \ldots Y_t$ can be restored within a predetermined error range.

16. The computer program product according to claim 15, wherein each of the first compressed data $Z_0, \ldots Z_t$ includes a parameter for a probability distribution of a latent variable that enables restoration of a respective one of the pre-treated medical images $Y_0, \ldots Y_t$ within the predetermined error range.

17. The computer program product according to claim 13, wherein the estimation of second compressed data $h_t$ comprises:

estimating the second compressed data $h_t$ by inputting the first compressed data $Z_0, \ldots Z_t$ to a recurrent neural network in an order corresponding to a time series order of the plurality of medical images $X_0, \ldots X_t$.

* * * * *